United States Patent [19]

Mondon-Rossignol et al.

[11] Patent Number: 5,702,689

[45] Date of Patent: Dec. 30, 1997

[54] USE OF AN ORGANOFLUORINE HYDROCARBON COMPOUND AS A BINDER FOR COSMETIC POWDER COMPOSITIONS, AND COMPOSITION CONTAINING SAID COMPOUND

[75] Inventors: Sylvie Mondon-Rossignol; Béatrice Defossez, both of Paris, France

[73] Assignee: L'Oreal, Paris, France

[21] Appl. No.: 374,716

[22] PCT Filed: May 25, 1994

[86] PCT No.: PCT/FR94/00616

§ 371 Date: Jan. 26, 1995

§ 102(e) Date: Jan. 26, 1995

[87] PCT Pub. No.: WO94/27559

PCT Pub. Date: Dec. 8, 1994

[30] Foreign Application Priority Data

May 26, 1993 [FR] France ................... 93/06326

[51] Int. Cl.$^6$ .................... A61K 7/021; A61K 7/031
[52] U.S. Cl. .................... 424/63; 424/64; 424/69; 514/937
[58] Field of Search .................... 424/63, 64, 69, 424/401; 514/937

[56] References Cited

U.S. PATENT DOCUMENTS 3,632,744   1/1972   Paulsen .

FOREIGN PATENT DOCUMENTS

| 0 469 602A1 | 2/1992 | European Pat. Off. . |
| 2 516 920 | 5/1983 | France . |
| 0545786A1 | 11/1992 | France . |
| WO93/11103 | 6/1993 | France . |
| 63-002916 | 1/1988 | Japan . |
| 5115769 | 5/1993 | Japan . |
| 5124933 | 5/1993 | Japan . |

*Primary Examiner*—Sally Gardner-Lane
*Attorney, Agent, or Firm*—Jacobson, Price, Holman & Stern, PLLC

[57] ABSTRACT

Cosmetic powder composition are disclosed which constitute a particulate phase and a greasy phase wherein the greasy phase comprises an organofluorine compound of the following formula (I) and wherein the particulate phase is free of such compound.

$$(R_F)_x-(A)_y-(R_H)_z \qquad (I)$$

where:

x represents 1, 2 or 3, y represents 0 or 1, and z represents 0, 1, 2 or 3, provided that y and z are not simultaneously zero and that when z is 0, x is 2 or 3;

$R_F$ represents an aliphatic or aromatic, saturated or unsaturated, linear, branched or cyclic fluorinated radical, in which the chain may be functionalized and/or interrupted by a divalent oxygen or sulfur atom, or a trivalent nitrogen atom and/or substituted by hydrogen atoms or halogen atoms other than fluorine atoms, provided that for any two carbon atoms of the backbone, no more than one of these substituents other than fluorine is present;

$R_H$ represents an aliphatic or aromatic, saturated or unsaturated, linear, branched or cyclic hydrocarbon radical, in which the chain may be functionalized and/or interrupted by one or more divalent oxygen or sulfur atoms, or one or more trivalent nitrogen atoms; and A represents a di-, tri- or tetravalent radical.

7 Claims, No Drawings

USE OF AN ORGANOFLUORINE HYDROCARBON COMPOUND AS A BINDER FOR COSMETIC POWDER COMPOSITIONS, AND COMPOSITION CONTAINING SAID COMPOUND

This application is a 371 of PCT/FR94/00616 filed May 25, 1994.

The present invention concerns the use of organofluorine hydrocarbon compounds as a binder in the preparation of cosmetic powder compositions, also a cosmetic composition in the form of an anhydrous powder comprising such compounds.

In the field of cosmetic powder compositions in the form of compressed or loose powders for face make-up or dusting powder, it is known to use a particulate phase comprising mainly pigments and fillers and a greasy phase comprising binders such as fatty substances to provide the finished product with a particular density, to bind the mineral and/or organic filler particles, to provide the make-up with smoothness and softness and to encourage adherence to the skin.

In order to provide suitable binding properties, a mixture of mineral and plant oils combined with fatty esters and/or fatty alcohols can be used. These mineral and plant oils can, however, produce cosmetic products which are not sufficiently smooth.

To overcome the problem of lack of smoothness, silicone oils or mixtures of silicone resins, waxes, oils or gums can be used. The use of silicone based products is, however, limited because of their incompatibility with some other oils and in particular, their insolubility in certain other oils.

Finally, certain perfluorinated oils, in particular perfluoropolyethers, are well known for providing smoothness to cosmetic compositions, but their use is limited due to their insolubility in the usual hydrocarbon oils (animal, vegetable or mineral) or in silicone oils. This insolubility results in instability in the cosmetic composition.

Of the known perfluoropolyethers, compounds of the type "FOMBLIN", in particular "FOMBLIN HC25", sold by MONTEDISON have the additional problem of poor pigment development: the shade produced by the pigment is relatively less intense, since FOMBLIN produces a white effect.

Thus, to obtain the desired shade with respect to a reference using a FOMBLIN compound, the pigment concentration must be increased by 25% or even 60%; apart from the additional costs involved, this reduces the concentration of mineral and/or organic fillers in the particulate phase, and the cosmetic formulation is more difficult to use; further, the color range is limited.

We have now developed cosmetic powder compositions in which the binder comprises an organofluorine hydrocarbon compound.

These cosmetic powder compositions both bind well and have excellent cosmetic properties: organofluorine hydrocarbon oils are good lubricants, are very smooth, spread well, provide the surface of compressed powders with a smooth and homogeneous appearance, and are adequately, even completely compatible with hydrocarbon oils or silicone oils. They also provide good pigment development.

For organofluorine hydrocarbon compounds, the substitution ratio for substitution of hydrogen atoms by fluorine atoms is defined by the ratio: number of fluorine atoms/ (number of fluorine atoms+number of hydrogen atoms), where only the hydrogen atoms which are bonded to carbon atoms of the backbone are taken into account.

The present invention thus concerns the use of organofluorine hydrocarbon compounds as a binder for cosmetic powder compositions; the organofluorine hydrocarbon compounds have a substitution ratio for hydrogen atoms bonded to carbon atoms by fluorine atoms of between 0.5% and 95%, preferably 10% to 80%.

In accordance with the invention, the compounds can be used in proportions of between 0.1% and 35% by weight with respect to the weight of the cosmetic powder composition.

Organofluorine hydrocarbon compounds of the invention have formula (I):

where:
x represents 1, 2 or 3,
y represents 0 or 1,
z represents 0, 1, 2 or 3,
provided that y and z are not simultaneously zero and that when z is 0, x is 2 or 3, $R_F$ represents an aliphatic or aromatic, saturated or unsaturated, linear, branched or cyclic fluorinated radical, in which the chain may be functionalized and/or interrupted by a divalent atom such as oxygen or sulfur, or a trivalent atom such as nitrogen and/or substituted by hydrogen atoms or other halogen atoms, provided that, for any two carbon atoms of the backbone, no more than one of these substituents other than fluorine is present, $R_H$ represents an aliphatic or aromatic, saturated or unsaturated, linear or branched or cyclic hydrocarbon radical, in which the chain may be functionalized and/or interrupted by one or more divalent atoms such as oxygen or sulfur, or one or more trivalent atoms such as nitrogen, A represents a di-, tri- or tetravalent radical such as

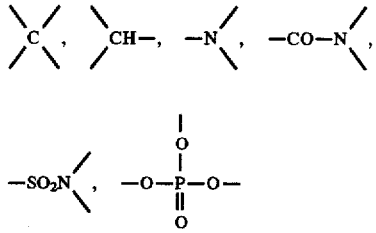

or cyclic, aliphatic or aromatic structures, or ethylenic unsaturations.

The term "functionalized" within the context of the present invention means an inserted, terminal or pendant substitution of the backbone by at least one functional group such as an alcohol, thiol, acid, carbonyl, sulfoxide, ester, amide, amine, phosphate, ethylene, acetylene, enamine or sulfonamide function.

The term "ethylenic unsaturation" means, for example,

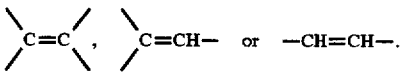

$R_H$ preferably represents a linear or branched $C_1$–$C_{22}$ alkyl radical or a mixture of linear or branched $C_1$–$C_{22}$ alkyl radicals, a $C_6$–$C_{10}$ aryl radical or a $C_7$–$C_{15}$ aralkyl radical.

$R_F$ preferably represents a perfluoroalkyl radical containing 4 to 22 carbon atoms.

Compounds which can be cited by way of example contain perfluorocarbon groups and hydrocarbon groups with a total number of carbon atoms of between 10 and 30, the number of carbon atoms of the hydrocarbon groups being equal to or greater than twice the number of carbon atoms of the perfluorocarbon groups, such as those described in Japanese patent JP 63-002916.

Compounds which can also be cited by way of illustration are the organofluorine hydrocarbon compounds in described patent application PCT/FR-92/01140, with a general structure as defined in the following formula (II):

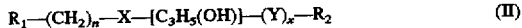

where
$C_3H_5(OH)$ represents the structures:

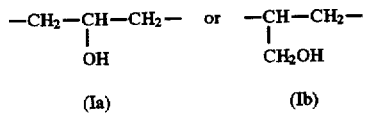

$R_1$ represents a perfluorine $C_4$-$C_{20}$ alkyl radical or a mixture of perfluorine $C_4$-$C_{20}$ alkyl radicals;

$R_2$ represents a linear or branched $C_1$-$C_{22}$ alkyl radical or a mixture of linear or branched $C_1$-$C_{22}$ alkyl radicals, a $C_6$-$C_{10}$ aryl radical or a $C_7$-$C_{15}$ aralkyl radical;

n is between 0 and 4;
X and Y represent O, S,

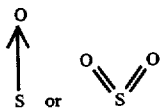

x represents 0 or 1;
provided that, when X is S,

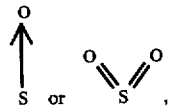

Y represents O.

These compounds can be prepared by reacting a fluorine compound with an acidic H with formula:

with an epoxide with formula:

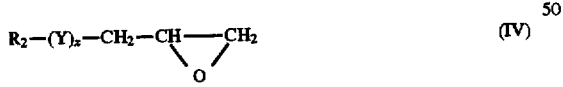

or reacting a hydrocarbon compound with an acidic H with formula:

with a fluorine-containing epoxide with formula:

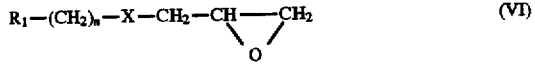

in the presence of a basic or acidic compound which acts as a reactant or as a catalyst, to produce the corresponding compound with formula (II), substituents $R_F$, $R_H$, n and x in the above formulae having the meanings given above for formula (II) and X and Y representing O or S, provided that when X is S, Y is O, and optionally oxidizing the mercaptan function to a sulfoxide or sulfone with an oxidizing agent, for example hydrogen peroxide in the presence of an acid, and recovering the compound obtained.

Examples of compounds with formula (II) are:
1-(2'-F-hexylethylthio)-3-(2"-ethylhexyloxy)-2-propanol,
1-(2'-F-octylethylthio)-3-(2"-ethylhexyloxy)-2-propanol,
1-(2'-F-octylethylthio)-3-butyloxy-2-propanol,
1-(2'-F-octylethylthio)-3-phenoxy-2-propanol,
1-(2'-F-hexylethylthio)-3-dodecyloxy-2-propanol,
1-(2'-F-hexylethylthio)-2-decanol,
1-(2'-F-hexylethylthio)-2-hexanol,
1-(2'-F-octylethylthio)-2-hexanol, and
1-(2'-F-hexylethylthio)-3-(2"-ethylhexyloxy)-2-propanol.

The products sold under the trade name "NOFABLE FO" by NIPPON OIL & CO with the following formula may also be cited:

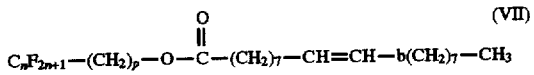

where n is a whole number equal to 6 or 8 and p is 1 or 2.

In addition, the compounds described in particular by B. Escoula in Synthetic Communications, 15(1), 35–38 (1985), can be cited. They have formula (VIII):

where:
R represents a butyl or phenyl radical, and
n is 4, 6 or 8.

Preferably, the organofluorine hydrocarbon compounds used are in the form of an oil or a wax.

The binder of the invention is constituted by the organofluorine hydrocarbon compounds described above which can be combined with hydrocarbon or silicone oils or waxes. These waxes or oils can be selected from:

mineral oils such as paraffin oil, vaseline oil or mineral oils with a boiling point of between 310° C. and 410° C.;

animal oils such as perhydrosqualene;

plant oils such as sweet almond oil, calophyllum oil, palm oil, avocado oil, jojoba oil, olive oil, castor oil, or cereal seed oils such as wheatgerm oil and corn oil;

synthetic esters such as Purcelin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propyleneglycol dicaprylate, or diisopropyl adipate;

volatile or non volatile silicone oils.

The waxes can be of plant, animal, mineral or synthetic origin, such as Carnauba wax, Candelilla wax, beeswax, whale wax, lanoline wax or microcrystalline wax.

Polyethylene waxes, preferably from homopolymers, should also be noted.

The organofluorine hydrocarbon compounds of the invention and other optional fatty substances constitute the greasy phase of the composition. This phase may also contain other compounds which are normally used in cosmetics, in particular solar filters, antioxidants, preservatives and active lipophiles.

The greasy phase of the composition can also contain thickening agents such as polybutene, polyalkyleneglycol, isopreneglycol, glycerol or sorbitol.

The total weight of the greasy phase is between 0.1% and 35% of the total composition weight.

According to the invention, the particulate phase is constituted by fillers and/or pigments which are normally used in cosmetic powder compositions, and can constitute 65% to 99.9% of the total composition weight, the complement being constituted by the greasy phase; the pigments can represent up to 80% by weight of the final composition.

The pigments are selected from inorganic and/or organic and/or pearlized pigments.

Examples of inorganic pigments are:

titanium dioxide (rutile or anatase), optionally surface treated, and codified in the Color Index under reference Cl 77891;

black, yellow, red and green iron oxides, codified under references Cl 77499, 77492, 77491;

manganese violet (Cl 77742);

ultramarine violet (Cl 77007);

ultramarine blue (Cl 77007);

chromium oxide (Cl 77288);

hydrated chromium oxide (Cl 77289); and ferric blue (Cl 77510).

Particular examples of organic pigments are:

D & C red No. 3 (Cl 45430:1);

D & C red No. 6 (Cl 15850:2);

D & C red No. 7 (Cl 15850:1);

D & C red No. 9 (Cl 15585:1);

D & C red No. 13 (Cl 15630:3);

D & C red No. 19 (Cl 45170);

D & C red No. 21 (Cl 45380:2);

D & C red No. 27 (Cl 45410:1);

D & C red No. 30 (Cl 73360);

D & C red No. 36 (Cl 12085);

carbon black (Cl 77266) and carmine and cochineal based lacquers (Cl 75470).

Pearlized pigments can be selected mainly from white pearlized pigments, such as mica coated with titanium oxide or bismuth oxychloride. Colored pearlized pigments can also be used, such as titanium mica colored with iron oxides, titanium mica colored with ferric blue or chromium oxide, titanium mica colored with an organic pigment of the type defined above, or bismuth oxychloride based pearlized pigments.

The fillers are particularly selected from:

talc, i.e. hydrated magnesium silicate, which can be used in the form of particles generally with dimensions of less than 40 µm; talc absorbs water and is primarily used for its unctuous feel;

micas, i.e. aluminosilicates of varying compositions, in the form of flakes with dimensions of 2 µm to 200 µm, preferably 5 µm to 70 µm, and a thickness of 0.1 µm to 5 µm, preferably 0.2 µm to 3 µm. Micas can be of natural origin (for example muscovite, margarite, roscoelite, liparite, biotite), or of synthetic origin;

modified or unmodified starch, in particular rice starch;

silica;

alumina;

boron nitride;

kaolin, i.e. hydrated aluminum silicate, in the form of isotropic particles;

zinc and titanium oxides which can be used as nanopigments;

bismuth oxychloride;

precipitated calcium carbonate, in particular particles with dimensions of less than about 10 µm;

magnesium carbonate or bicarbonate;

metallic soaps derived from organic carboxylic acids containing 8 to 22 carbon atoms, preferably 12 to 18 carbon atoms, for example zinc, magnesium or lithium stearate, zinc laurate, or magnesium myristate. These soaps are generally in the form of particles with dimensions of less than 10 µm;

powdered synthetic polymers (or copolymers) selected from polyethylene and its derivatives, for example polytetrafluoroethylene or polystyrene, polyacrylates, polymethacrylates, polyesters or polyamides, in particular powdered nylon;

hollow microspherical powders formed of synthetic thermoplastics material, the hollow portion containing a gas.

The hollow microspheres are prepared using known processes, such as those described in U.S. Pat. No. 3,615,972 or European patent application EP-A-0 056 219.

These microspheres can be manufactured from any non-toxic, non-irritating material. These materials can, for example, be polymers or copolymers of ethylene derivatives, for example polyethylene, polystyrene, vinyl chloride—acrylonitrile copolymer, polyesters, urea—formaldehyde polymers, or vinylidene chloride copolymers, for example vinylidene chloride—acrylonitrile copolymer.

The fillers can represent up to 95% of the total weight of the composition of the invention.

In addition, substances such as amino acids, metallic soaps, silicones or fluorine-containing compounds, can be used to coat the pigments and the fillers to modify their surface properties.

The present invention also concerns a cosmetic powder composition comprising a greasy phase and a particulate phase comprising pigments and/or fillers, characterized in that it comprises 98.99% to 65% by weight of particulate phase and 1.01% to 35% by weight of at least one organofluorine hydrocarbon compound with a substitution ratio of hydrogen atoms bonded to carbon atoms by fluorine atoms of between 0.5% and 95%.

Preferably, the compositions of the invention comprise 3% to 15% by weight of the organofluorine hydrocarbon compound, with respect to the total composition weight.

Compositions of the invention are mainly in the form of eyeshadows, blushers, compressed or loose powders for face make-up, or in the form of dusting powders.

Depending on whether the powders are compressed or not, they are prepared using one of the two methods described below.

A compressed powder is prepared by mixing, in a first step, the pigments and/or fillers, also the powdered additives, then the binder is added and, optionally, the thickening agents, then the other optional ingredients, and the whole is mixed and/or optionally ground.

The binder can be heated if necessary.

The mixture is then compressed into metal trays using a press.

In order to prepare loose powder, the pigments and/or fillers and the powdered additives are mixed, then the binder is added and optionally, thickening agents and other optional ingredients are added, then the whole is mixed and optionally ground.

The binder is heated if necessary. If desired, the mixture can be sieved before packing into a suitable receptacle.

PREPARATION EXAMPLES

Example I 1-(2'-F-hexylethylthio)-3-(2"-ethylhexyloxy)-2-propanol 3.6 g of a methanolic solution of sodium methylate (about 30%-5.54 meq g$^{-1}$) was added to 152 g of 2-F-hexylethanethiol over one minute at a temperature of 25° C., with stirring and in a stream of nitrogen.

The mixture was heated to 70° C. The methanol present in the mixture was evaporated off under vacuum.

The 2-ethylhexylglycidylether (74.4 g) was added dropwise over one hour. The temperature of the mixture was maintained at 60° C. to 70° C. during addition of the epoxide.

After addition, the temperature was reduced to 25° C.

The mixture was neutralized using 20 ml of normal HCl.

1-(2'-F-hexylethylthio)-3-(2"-ethylhexyloxy)-2-propanol was separated by distillation: B Pt=141° C./66.5 Pa.

175 g (77%) of a colorless translucent oil was obtained. Elemental analysis

|  | % C | % H | % S | % F |
| --- | --- | --- | --- | --- |
| Calculated | 40.28 | 4.80 | 5.66 | 43.60 |
| Measured | 40.37 | 4.82 | 5.55 | 43.74 |

Example II 1-(2'-F-octylethylthio)-3-(2"-ethylhexyloxy)-2-propanol

The compound was prepared in analogous fashion to the preparation described for Example I using:

288 g of 2-F-octylethanethiol;

5.4 g of a methanolic sodium methylate solution (5.54 meq g$^{-1}$);

111.6 g of 2-ethylhexylglycidylether;

30 ml of normal HCl.

337 g (81%) of a colorless translucent oil was obtained. Elemental analysis

|  | % C | % H | % S | % F |
| --- | --- | --- | --- | --- |
| Calculated | 37.84 | 4.08 | 4.81 | 48.46 |
| Measured | 37.83 | 4.06 | 4.20 | 47.45 |

FORMULATION EXAMPLES

Example 1

| Eyeshadow | Parts by weight |
| --- | --- |
| Part A: | |
| Mica | 20.0 |
| Titanium dioxide | 2.0 |
| Zinc stearate | 3.0 |
| Powdered polyamide | 10.0 |
| Black iron oxide | 3.6 |
| Manganese violet | 9.6 |
| Talc | 45.1 |
| Part B: | |
| 1-(2'-F-hexylethylthio)-3-(2"-ethylhexyloxy)-2-propanol | 4.0 |
| Vaseline oil | 0.5 |
| Castor oil | 2.0 |
| Preservative | 0.2 |
| | 100.0 |

Method

The phase A constituents were mixed together and the phase B constituents were mixed together, then phase B was added to phase A and mixed again; this was ground if necessary, sieved and compressed into a metallic tray.

The product obtained was very smooth.

Example 2

| Eyeshadow | Parts by weight |
| --- | --- |
| Part A: | |
| Bismuth oxychloride | 8.0 |
| Zinc stearate | 3.0 |
| Mica | 20.0 |
| Chromium oxide | 5.4 |
| Iron oxides | 9.1 |
| Talc | 48.3 |
| Part B: | |
| Organofluorine hydrocarbon oil (NOFABLE-FO 9982, sold by NIPPON OIL & FATS) | 4.5 |
| Jojoba oil | 1.5 |
| Preservative | 0.2 |
| | 100.0 |

The product was obtained using the method described for Example 1; it bound well and had good pigment development.

Example 3

| Eyeshadow | Parts by weight |
| --- | --- |
| Part A: | |
| Bismuth oxychloride | 10.0 |
| Mica | 20.0 |
| Titanium dioxide | 2.0 |
| Iron oxides | 15.5 |
| Talc | 46.0 |
| Part B: | |
| 1-(2'-F-hexylethylthio)-3-(2"-ethylhexyloxy)-2-propanol | 6.5 |
| | 100.0 |

The composition obtained, using the method described for Example 1, was very smooth and very easy to distribute; it produced a homogeneous make-up.

Example 4

| Eyeshadow | Parts by weight |
|---|---|
| Part A: | |
| Bismuth oxychloride | 10.0 |
| Mica | 20.0 |
| Zinc stearate | 3.0 |
| Black iron oxide | 3.6 |
| Manganese violet | 9.6 |
| Ultramarine blue | 10.8 |
| DC Red 30 | 1.8 |
| Talc | 34.7 |
| Part B: | |
| 1-(2'-F-hexylethylthio)-3-(2"-ethylhexyloxy)-2-propanol | 6.5 |
| | 100.0 |

The product was obtained using the method described for Example 1.

Example 5

Comparative

| Eyeshadow | Parts by weight |
|---|---|
| Part A: | |
| Bismuth oxychloride | 10.0 |
| Mica | 20.0 |
| Zinc stearate | 3.0 |
| Black iron oxide | 3.6 |
| Manganese violet | 9.6 |
| Ultramarine blue | 10.8 |
| DC Red 30 | 1.8 |
| Talc | 34.7 |
| Part B: | |
| Perfluoropolyether oil (FOMBLIN HC25 - MONTEDISON) | 6.5 |
| | 100.0 |

The product was obtained using the method described for Example 1.

Compared with Example 5, the color of Example 4 was more intense in the tray and had no white background due to good pigment development.

In order to obtain the shade obtained in Example 4, the pigment concentration in Example 5 had to be increased by 29.8%.

Example 6

| Eyeshadow | Parts by weight |
|---|---|
| Part A: | |
| Bismuth oxychloride | 10.0 |
| Mica | 20.0 |
| Zinc stearate | 3.0 |
| Chromium oxide | 5.4 |
| Black iron oxide | 5.9 |
| Yellow iron oxide | 3.2 |
| Talc | 46.0 |
| Part B: | |
| 1-(2'-F-hexylethylthio)-3-(2"-ethylhexyloxy)-2-propanol | 6.5 |
| | 100.0 |

The product was obtained using the method described for Example 1.

Example 7

Comparative

| Eyeshadow | Parts by weight |
|---|---|
| Part A: | |
| Bismuth oxychloride | 10.0 |
| Mica | 20.0 |
| Zinc stearate | 3.0 |
| Chromium oxide | 5.4 |
| Black iron oxide | 5.9 |
| Yellow iron oxide | 3.2 |
| Talc | 46.0 |
| Part B: | |
| Perfluoropolyether oil (FOMBLIN HC25 - MONTEDISON) | 6.5 |
| | 100.0 |

Compared with Example 7, the color of Example 6 was more intense in the tray and had no white background, due to good pigment development.

In order to obtain the shade obtained in Example 6, the pigment concentration in Example 7 had to be increased by 58.6%.

Example 8

| Blusher | Parts by weight |
|---|---|
| Part A: | |
| Talc | 70.8 |
| Titanium dioxide | 5.0 |
| Mica | 10.0 |
| Zinc stearate | 2.0 |
| DC Red 30 | 0.5 |
| Iron oxides | 6.0 |
| Part B: | |
| 1-(2'-F-hexylethylthio)-3-(2"-ethylhexyloxy)-2-propanol | 4.5 |
| Castor oil | 0.5 |
| Preservative | 0.2 |
| Fragrance | 0.3 |
| | 100.0 |

The product was obtained using the method of Example 1.

Example 9

| Compressed face powder | Parts by weight |
| --- | --- |
| Part A: | |
| Sericite | 65.8 |
| Mica | 15.0 |
| Powdered polyethylene | 5.0 |
| Titanium dioxide | 2.0 |
| Iron oxides | 8.0 |
| Part B: | |
| 1-(2'-F-hexylethylthio)-3-(2"-ethylhexyloxy)-2-propanol | 5.5 |
| Jojoba oil | 1.0 |
| Preservative | 0.2 |
| Fragrance | 0.3 |
| | 100.0 |

The product was obtained using the method of Example 1 and was very smooth.

Example 10

| Loose face powder | Parts by weight |
| --- | --- |
| Part A: | |
| Talc | 93.35 |
| Iron oxide | 0.7 |
| Titanium dioxide | 2.0 |
| Part B: | |
| 1-(2'-F-hexylethylthio)-3-(2"-ethylhexyloxy)-2-propanol | 3.0 |
| Vaseline oil | 0.75 |
| Fragrance | 0.2 |
| | 100.0 |

The constituents of Part A were mixed together then the premixed constituents of part B were incorporated by mixing, followed by sieving.

Example 11

| Eyeshadow | Parts by weight |
| --- | --- |
| Part A: | |
| Talc | 58.2 |
| Yellow iron oxide | 0.3 |
| Black iron oxide | 0.1 |
| Brown iron oxide | 0.2 |
| Part B: | |
| Titanium mica | 30 |
| Part C: | |
| 1-(2'-F-hexylethylthio)-3-(2"-ethylhexyloxy)-2-propanol | 10 |
| Castor oil | 1 |
| Preservative | 0.2 |
| | 100.0 |

Method

The constituents of phase A were mixed, then the constituents of phase C. Phase C was added to phase A and mixed again; grinding was optional. Phase B was added and mixed again. This was then sieved and compressed into a metallic tray.

Example 12

| Blusher | Parts by weight |
| --- | --- |
| Part A: | |
| Titanium dioxide | 6.0 |
| Zinc stearate | 2.0 |
| Mica | 10.0 |
| DC Red 30 | 0.6 |
| Iron oxides | 38.0 |
| Talc | 73.1 |
| Part B: | |
| 1-(2'-F-octylethylthio)-3-(2"-ethylhexyloxy)-2-propanol | 6.5 |
| | 100.0 |

The product was obtained using the method described in Example 1.

We claim:

1. A cosmetic powder composition constituted by a particulate phase comprising pigments and/or fillers and a greasy phase, wherein the greasy phase represents 1.01% to 35% by weight of the total composition weight and comprises 0.1% to 15% by weight of at least one organofluorine hydrocarbon compound having a ratio of hydrogen atoms bonded to carbon atoms substituted by fluorine atoms ranging from 0.5% to 95%, and 98.99% to 65% by weight of a particulate phase free of fluorine compound comprising pigments and/or fillers, the organofluorine hydrocarbon compound having formula (I):

$$(R_F)_x—(A)_y—(R_H)_z \qquad (I)$$

where:

x represents 1, 2 or 3, y represents 0 or 1, and z represents 0, 1, 2 or 3, provided that y and z are not simultaneously zero and that when z is 0, x is 2 or 3;

$R_F$ represents an aliphatic or aromatic, saturated or unsaturated, linear, branched or cyclic fluorinated radical, in which the chain may be functionalized and/or interrupted by a divalent oxygen or sulfur atom, or a trivalent nitrogen atom and/or substituted by hydrogen atoms or halogen atoms other than fluorine atoms, provided that for any two carbon atoms of the backbone, no more than one of these substituents other than fluorine is present;

$R_H$ represents an aliphatic or aromatic, saturated or unsaturated, linear, branched or cyclic hydrocarbon radical, in which the chain may be functionalized and/or interrupted by one or more divalent oxygen or sulfur atoms, or one or more trivalent nitrogen atoms; and A represents a di-, tri- or tetravalent radical selected from the group consisting of:

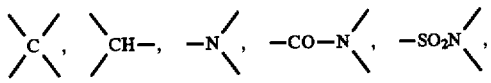

-continued

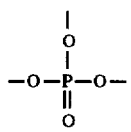

and ethylenic unsaturations.

2. A cosmetic composition according to claim 1 wherein the organofluorine hydrocarbon compound has a ratio of hydrogen atoms bonded to carbon atoms substituted by fluorine atoms ranging from 10% to 80%.

3. A cosmetic composition according to claim 1 characterized in that the organofluorine hydrocarbon compound has formula (II):

$$R_1-(CH_2)_n-X-[C_3H_5(OH)]-(Y)_x-R_2 \qquad (II)$$

where $C_3H_5(OH)$ represents the structures:

$R_1$ represents a perfluorine $C_4-C_{20}$ alkyl radical or a mixture of perfluorine $C_4-C_{20}$ alkyl radicals;

$R_2$ represents a linear or branched $C_1-C_{22}$ alkyl radical or a mixture of linear or branched $C_1-C_{22}$ alkyl radicals, a $C_6-C_{10}$ aryl radical or a $C_7-C_{15}$ aralkyl radical;

n is between 0 and 4;

X and Y represent O, S,

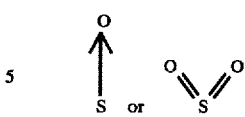

x represents 0 or 1;

provided that, when X is S,

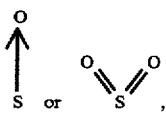

represents O.

4. A cosmetic composition according to claim 1 comprising 3% to 15% by weight of organofluorine hydrocarbon compound with respect to the total composition weight.

5. A cosmetic composition according to claim 1 wherein, apart from the organofluorine hydrocarbon compound, the greasy phase comprises at least one hydrocarbon or silicone oil or wax.

6. A cosmetic composition according to claim 1 in the form of an eyeshadow, blusher, compressed or loose face powder or compressed or loose body powder.

7. A cosmetic composition according to claim 1, wherein the greasy phase represents 3 to 15% of the total composition weight.

* * * * *